United States Patent
Breillatt, Jr. et al.

(10) Patent No.: US 6,824,688 B2
(45) Date of Patent: Nov. 30, 2004

(54) BLOOD COLLECTION SYSTEMS AND METHODS USING A POROUS MEMBRANE ELEMENT

(75) Inventors: Julian P. Breillatt, Jr., Mundelein, IL (US); Shmuel Sternberg, Palatine, IL (US)

(73) Assignee: Baxter International Inc., Deerfield, IL (US)

(*) Notice: Subject to any disclaimer, the term of this patent is extended or adjusted under 35 U.S.C. 154(b) by 0 days.

(21) Appl. No.: 10/606,589

(22) Filed: Jun. 26, 2003

(65) Prior Publication Data

US 2003/0234226 A1 Dec. 25, 2003

Related U.S. Application Data

(62) Division of application No. 09/624,308, filed on Jul. 24, 2000, now Pat. No. 6,612,447.

(51) Int. Cl.[7] .............................................. B01D 37/00
(52) U.S. Cl. ........................................ 210/649; 210/650
(58) Field of Search .......................... 210/252, 257.1, 210/435, 483, 489, 500.21, 649, 650, 767, 488; 435/2

(56) References Cited

U.S. PATENT DOCUMENTS

| | | |
|---|---|---|
| 4,612,119 A | 9/1986 | Eguchi |
| 4,629,563 A | 12/1986 | Wrasidlo |
| 4,701,267 A | 10/1987 | Watanabe et al. |
| 4,774,039 A | 9/1988 | Wrasidlo |
| 4,840,733 A | 6/1989 | Sasaki et al. |
| 4,900,443 A | 2/1990 | Wrasidlo |
| 4,900,449 A | 2/1990 | Kraus et al. |
| 4,902,422 A | 2/1990 | Pinnau et al. |
| 4,925,572 A | 5/1990 | Pall |
| 4,933,081 A | 6/1990 | Sasaki et al. |
| 4,933,085 A | 6/1990 | Kneifel et al. |
| 4,964,990 A | 10/1990 | Kraus et al. |
| 4,983,288 A | 1/1991 | Karbachsch et al. |
| 4,985,153 A | 1/1991 | Kuroda et al. |
| 5,071,448 A | 12/1991 | Bikson et al. |
| 5,076,935 A | 12/1991 | Kraus et al. |
| 5,089,192 A | 2/1992 | Costa |
| 5,102,917 A | 4/1992 | Bedwell et al. |
| 5,108,607 A | 4/1992 | Kraus et al. |

(List continued on next page.)

FOREIGN PATENT DOCUMENTS

| | | |
|---|---|---|
| EP | 272841 | 6/1988 |
| EP | 406485 | 1/1991 |
| EP | 408462 B1 A2 | 1/1991 |
| EP | 419346 | 3/1991 |
| EP | 378684 | 3/1994 |

OTHER PUBLICATIONS

Brull et al, Asymmetric membrane filters for the removal of leukocytes from blood, Journal of Biomedical Materials Research, vol. 25, 1459–1480 (1991).

*Primary Examiner*—John Kim
(74) *Attorney, Agent, or Firm*—Joseph B. Barrett; Daniel D. Ryan

(57) ABSTRACT

A filter for removing leukocytes from blood comprises a filter media enclosed in a housing. The filter media includes a main filter region comprising a porous membrane structure extending between first and second skin surfaces. The porous membrane structure is formed by intersecting cells having a range of diameters. The cells adjacent to the first skin surface have diameters generally smaller than the diameters of the cells adjacent to the second skin surface. The first skin surface includes an open area defined by pores, which are formed by the intersection of cells with the first skin surface. The majority of the open area is defined by pores having a diameter of between about 12 μm and 28 μm.

2 Claims, 8 Drawing Sheets

U.S. PATENT DOCUMENTS

| | | |
|---|---|---|
| 5,164,087 A | 11/1992 | Naoi et al. |
| 5,171,445 A | 12/1992 | Zepf |
| 5,188,734 A | 2/1993 | Zepf |
| 5,234,593 A | 8/1993 | Kuroki et al. |
| 5,344,561 A | 9/1994 | Pall et al. |
| 5,407,581 A | 4/1995 | Onodera et al. |
| 5,443,743 A | 8/1995 | Gsell |
| 5,456,835 A | 10/1995 | Castino et al. |
| 5,476,587 A | 12/1995 | Kuroki et al. |
| 5,478,470 A | 12/1995 | Fukuda et al. |
| 5,498,336 A | 3/1996 | Katsurada et al. |
| 5,543,062 A | 8/1996 | Nishimura |
| 5,665,233 A | 9/1997 | Fukuda et al. |
| 5,698,281 A | 12/1997 | Bellantoni et al. |
| 5,707,520 A | 1/1998 | Kuroki et al. |
| 5,707,526 A | 1/1998 | Kraus et al. |
| 5,783,094 A | 7/1998 | Kraus et al. |
| 5,820,755 A | 10/1998 | Kraus et al. |
| 5,834,107 A | 11/1998 | Wang et al. |
| 5,846,422 A | 12/1998 | Ditter et al. |
| 5,869,174 A | 2/1999 | Wang |
| 5,886,059 A | 3/1999 | Wang |
| 5,895,575 A | 4/1999 | Kraus et al. |
| 5,906,742 A | 5/1999 | Wang et al. |
| 5,928,774 A | 7/1999 | Wang et al. |
| 5,958,989 A | 9/1999 | Wang et al. |
| 5,979,670 A | 11/1999 | Ditter et al. |
| 6,008,059 A | 12/1999 | Schrier et al. |
| 6,013,184 A | 1/2000 | Fukuda et al. |
| 6,032,807 A | 3/2000 | Sternberg et al. |
| 6,045,701 A | 4/2000 | Ung-Chhun et al. |
| 6,045,899 A | 4/2000 | Wang et al. |
| 6,056,903 A | 5/2000 | Greenwood et al. |
| 6,367,634 B1 | 4/2002 | Lynn et al. |

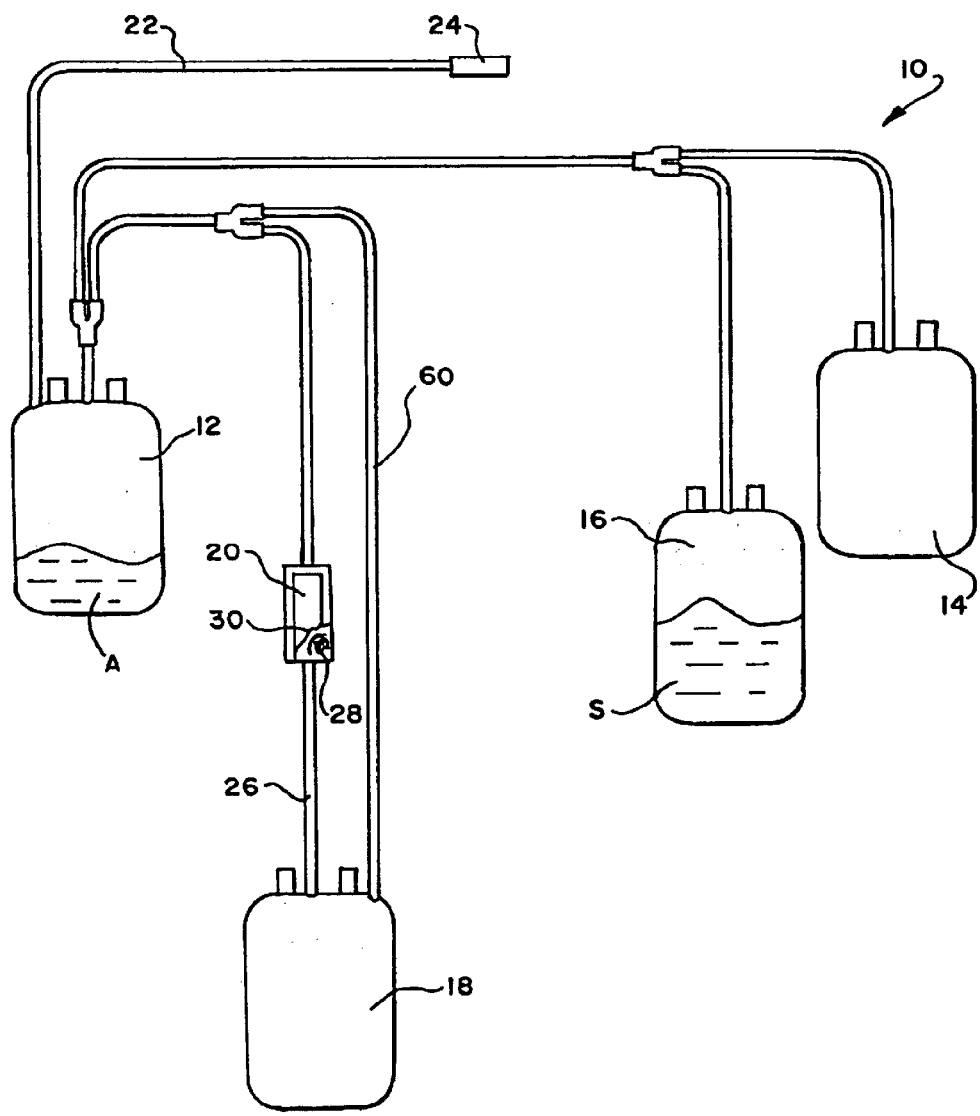

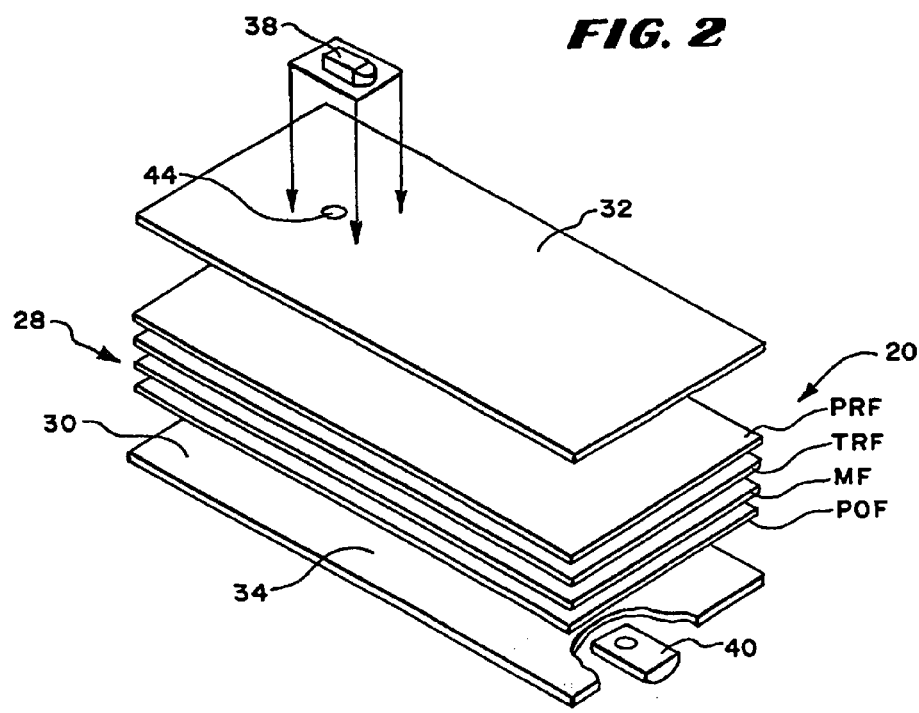
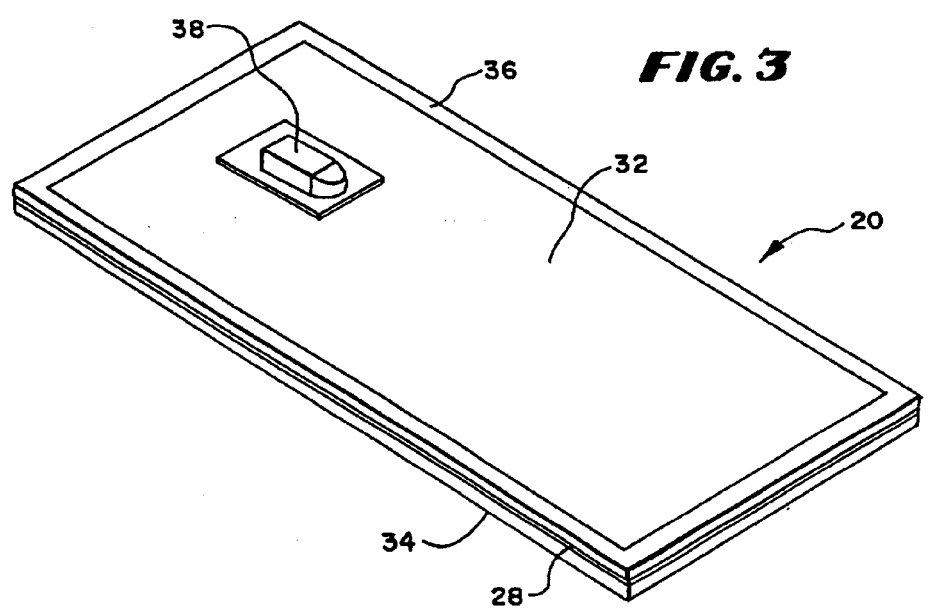

BLOOD COLLECTION SYSTEMS AND METHODS USING A POROUS MEMBRANE ELEMENT

RELATED APPLICATIONS

This application is a divisional of U.S. patent application Ser. No. 09/624,308 flied 24 Jul. 2000, now issued as U.S. Pat. No. 6,612,447.

FIELD OF THE INVENTION

The invention generally relates to blood collection and processing systems and methods.

BACKGROUND OF THE INVENTION

Systems composed of multiple, interconnected plastic bags have met widespread use and acceptance in the collection, processing and storage of blood components. Using these systems, whole blood is collected and separated into its clinical components (typically red blood cells, platelets, and plasma). The components are individually stored and used to treat a multiplicity of specific conditions and diseased states.

Before storing blood components for later transfusion, it is believed to be desirable to minimize the presence of impurities or other materials that may cause undesired side effects in the recipient. For example, because of possible reactions, it is generally considered desirable to remove substantially all the leukocytes from blood components before storage, or at least before transfusion.

Filtration is conventionally used to accomplish leuko-reduction. Systems and methods for reducing the number of leukocytes by filtration in multiple blood bag configurations are described, e.g., in Stewart U.S. Pat. No. 4,997,577, Stewart et al. U.S. Pat. No. 5,128,048, Johnson et al. U.S. Pat. No. 5,180,504, and Bellotti et. al. U.S. Pat. No. 5,527,472.

SUMMARY OF THE INVENTION

One aspect of the invention provides systems and methods for removing leukocytes from blood using a filter media having a main filter region comprising a porous membrane structure extending between first and second skin surfaces. The porous membrane structure is formed by intersecting cells having a range of diameters. The cells adjacent to the first skin surface have diameters generally smaller than the diameters of the cells adjacent to the second skin surface. The first skin surface includes an open area defined by pores, which are formed by the intersection of cells with the first skin surface. The majority of the open area is defined by pores having a diameter of between about 12 $\mu$m and 28 $\mu$m.

In one embodiment, the main filter region includes a polyethersulfone material.

In one embodiment, the filter media is enclosed in a housing. The housing comprises first and second flexible sheets made of a meltable material. A peripheral seal joins the sheets directly to the filter media to encapsulate the filter media between the first and second sheets. The seal includes a commingled melted matrix comprising material of the sheets and material of the filter media.

Another aspect of the invention provides systems and methods for removing leukocytes from blood using a filter media having a main filter region. The main filter region comprises a layered porous membrane structure that includes several regions of larger pore sizes alternating in the direction of flow with several regions of smaller pore sizes, or vice versa. Blood traversing the main filter region thereby passes in succession through several alternating regions of smaller, then larger, then smaller diameter pores, or vice versa.

Other features and advantages of the invention will become apparent upon review of the following description, drawings, and appended claims.

BRIEF DESCRIPTION OF THE DRAWINGS

FIG. 1 is a schematic view of a blood collection and storage system that includes a filter that embodies features of the invention and that removes leukocytes from red blood cells;

FIG. 2 is an exploded perspective view of the filter that forms a part of the system shown in FIG. 1;

FIG. 3 is an assembled perspective view of the filter shown in FIG. 2;

Figure 4:
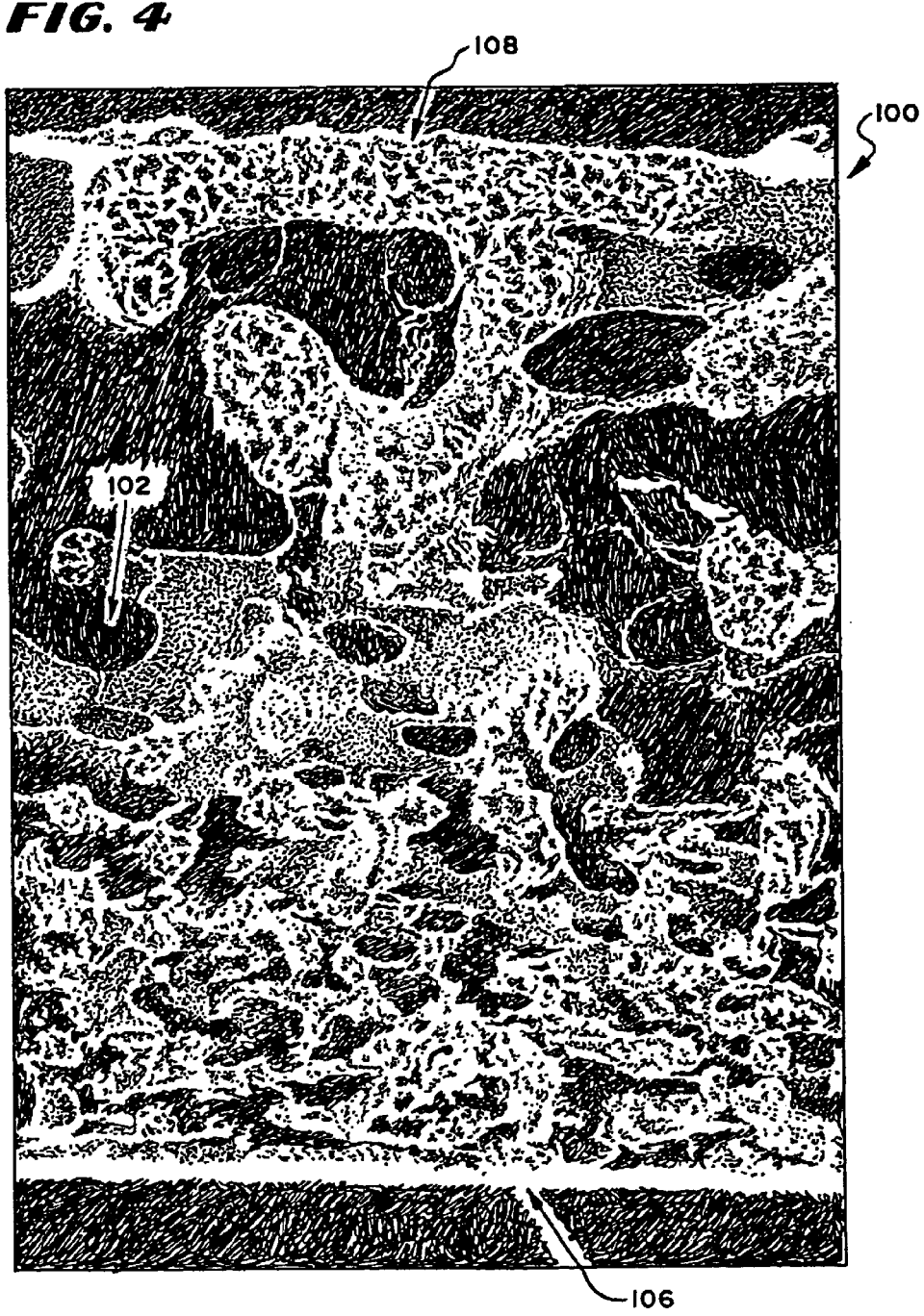
FIG. 4 is a side section SEM (×900) view showing a membrane that the filter shown in FIG. 3 incorporates as its main filter for removing leukocytes.

The invention is not limited to the details of the construction and the arrangements of parts set forth in the following description or shown in the drawings. The invention can be practiced in other embodiments and in various other ways. The terminology and phrases are used for description and should not be regarded as limiting.

DESCRIPTION OF THE PREFERRED EMBODIMENTS

FIG. 1 shows a blood collection and storage system 10 having an integral flexible filter 20. The filter 20 can be incorporated into various types of blood collection systems, and representative examples of such systems will be described.

In FIG. 1, the system 10 provides red blood cells for long term storage that are substantially free of leukocytes. The system 10 also provides platelet concentrate and the platelet-poor plasma for long term storage. The blood collection and storage assembly 10, once sterilized, constitutes a sterile, "closed" system, as judged by the applicable standards in the United States. The system 10 is a disposable, single use item.

As shown in FIG. 1, the system 10 includes a primary bag 12 and three transfer bags or containers 14, 16, and 18. Like the flexible filter 20, the transfer bags 14, 16, and 18 are integrally attached to the system 10.

In use, the system 10 is manipulated in conventional ways. The primary bag 12 (which is also called a donor bag) receives whole blood from a donor through integrally attached donor tube 22 that carries an phlebotomy needle 24. A suitable anticoagulant A is contained in the primary bag 12. The whole blood is centrifugally separated by convention means inside the primary bag 12 into red blood cells and platelet-rich plasma. Leukocytes dwell in the interface between the red blood cells and platelet-rich plasma.

The transfer bag 14 is intended to receive platelet-rich plasma separated from the whole blood collected in the primary bag 12. Attempts are made when transferring the platelet-rich plasma out of the primary bag 12 to keep as many leukocytes in the primary bag 12 as possible. The transfer of platelet-rich plasma into the transfer bag 14 leaves the red blood cells and the leukocytes behind in the primary bag 12.

The transfer bag 16 contains a suitable storage solution S for red blood cells. One such solution is disclosed in Grode et al U.S. Pat. No. 4,267,269, which is sold by Baxter Healthcare Corporation under the brand name ADSOL® Solution. The storage solution S is transferred into the primary bag 12 after transfer of the platelet-rich plasma into the transfer bag 14.

The platelet-rich plasma is centrifugally separated by conventional means in the transfer bag 14 into platelet concentrate and platelet-poor plasma. The platelet-poor plasma is transferred into the transfer bag 16, which is now emptied of storage solution S. The transfer bag 16 serves as the storage container for the platelet-poor plasma. The transfer bag 14 serves as its storage container for the platelet concentrate.

The storage solution S is mixed with the red blood cells and leukocytes remaining in the primary bag 12. The mixture of storage solution S, red blood cells, and leukocytes is transferred from the primary bag 12 through tubing 26. The tubing 26 carries in-line the integral, flexible filter 20. The flexible filter 20 includes a filtration medium 28 contained within a housing 30. The filtration medium is selected to remove leukocytes from red blood cells.

The leukocyte-reduced red blood cells enter the transfer bag 18. The transfer bag 18 serves as the storage container for the leukocyte-reduced red blood cells. Prior to storage, residual air in the transfer bag 18 can be vented into the primary bag 12 through tubing 60.

The bags and tubing associated with the processing system 10 can all be made from conventional approved medical grade plastic materials, such as polyvinyl chloride plasticized with di-2-ethylhexylphthalate (PVC-DEHP). The bags are formed using conventional heat sealing technologies, e.g., radio frequency (RF) heat sealing.

Alternatively, since the transfer bag 14 is intended to store the platelet concentrate, it can be made of polyolefin material (as disclosed in Gajewski et al U.S. Pat. No. 4,140,162) or a polyvinyl chloride material plasticized with tri-2-ethylhexyl trimellitate (TEHTM). These materials, when compared to DEHP-plasticized polyvinyl chloride materials, have greater gas permeability that is beneficial for platelet storage.

The flexible filter 20, like the rest of the system 10, is a disposable, single use item. Also, like the rest of the system 10, the filter housing 30 is made using conventional approved medical grade plastic materials. Furthermore, like the rest of the system 10, the filter housing 30 is formed using conventional radio frequency heat sealing technology. The filter 20, being flexible, facilitates handling and reduces the incidence of damage to other components of the system 10 during centrifugal processing.

In the illustrated embodiment (see FIGS. 2 and 3), the filter housing 30 comprising first and second sheets 32 and 34 of medical grade plastic material, such as polyvinyl chloride plasticized with di-2-ethylhexylphthalate (PVC-DEHP). Other medical grade plastic materials can be used that are not PVC and/or are DEHP-free, provided that the material heats and flows when exposed to radio frequency energy.

As FIG. 2 best shows, the filtration medium 28 comprises, in the blood flow direction, a prefilter region PRF, a transfer filter region TRF, a main filter region MF, and a postfilter region POF. The regions are sandwiched between the sheets 32 and 34 and joined along a continuous peripheral seal 36 (as FIG. 3 shows).

The prefilter region PRF and postfilter region POF can be made of fibrous material, e.g., include melt blown or spun bonded synthetic fibers (e.g., nylon or polyester or polyethylene or polypropylene), semi-synthetic fibers, regenerated fibers, or inorganic fibers. The prefilter and postfilter regions PRF and POF desirably have a pore size and fiber diameter not well suited for leukocyte removal. Instead, the fibrous material of the prefilter region PRF is sized to remove gross clots and aggregations present in the blood. The fibrous material of the postfilter region POF is sized to provide a fluid manifold effect at the outlet of the filter. In a representative embodiment, the material of the prefilter region PRF has a pore size of between about 15 $\mu$m to about 20 $\mu$m, and the material of the postfilter region POF has a pore size of about 20 $\mu$m.

The transfer region TR is made of fibrous material (e.g., polyethylene) having a fiber diameter less than the fiber diameter of the prefilter region PRF. In a representative embodiment, the material of the prefilter region PRF possesses an average fiber diameter of about 12 $\mu$m, and the material of the transfer filter region TFR possesses a fiber diameter of about 4 $\mu$m. Preferably, the fibrous material of the transfer filter region TFR is also coated with a polymer material including polyalkylene oxide (PEO), such as disclosed in U.S. Pat. No. 6,045,701, which is incorporated herein by reference.

Preferably, the fibrous material of the transfer region TFR is arranged in more than a single layer. In a preferred embodiment, a transfer filter region TFR comprises four formed layers, each having an individual thickness in the flow direction of about 0.4 mm.

Figure 5:
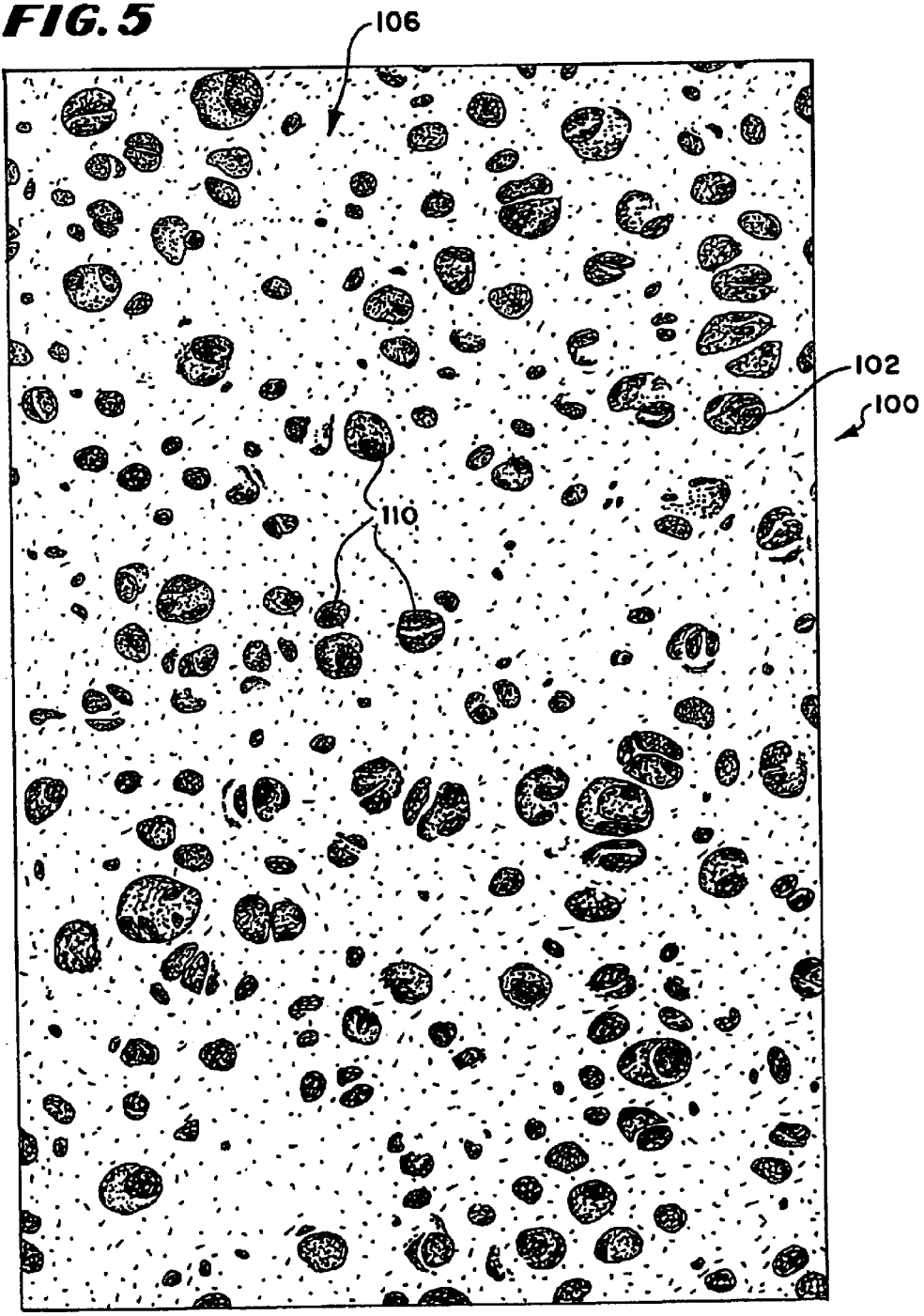
FIG. 5 is a plane SEM view (×400) of the downstream skin surface of the membrane shown in FIG. 4.
Figure 6:
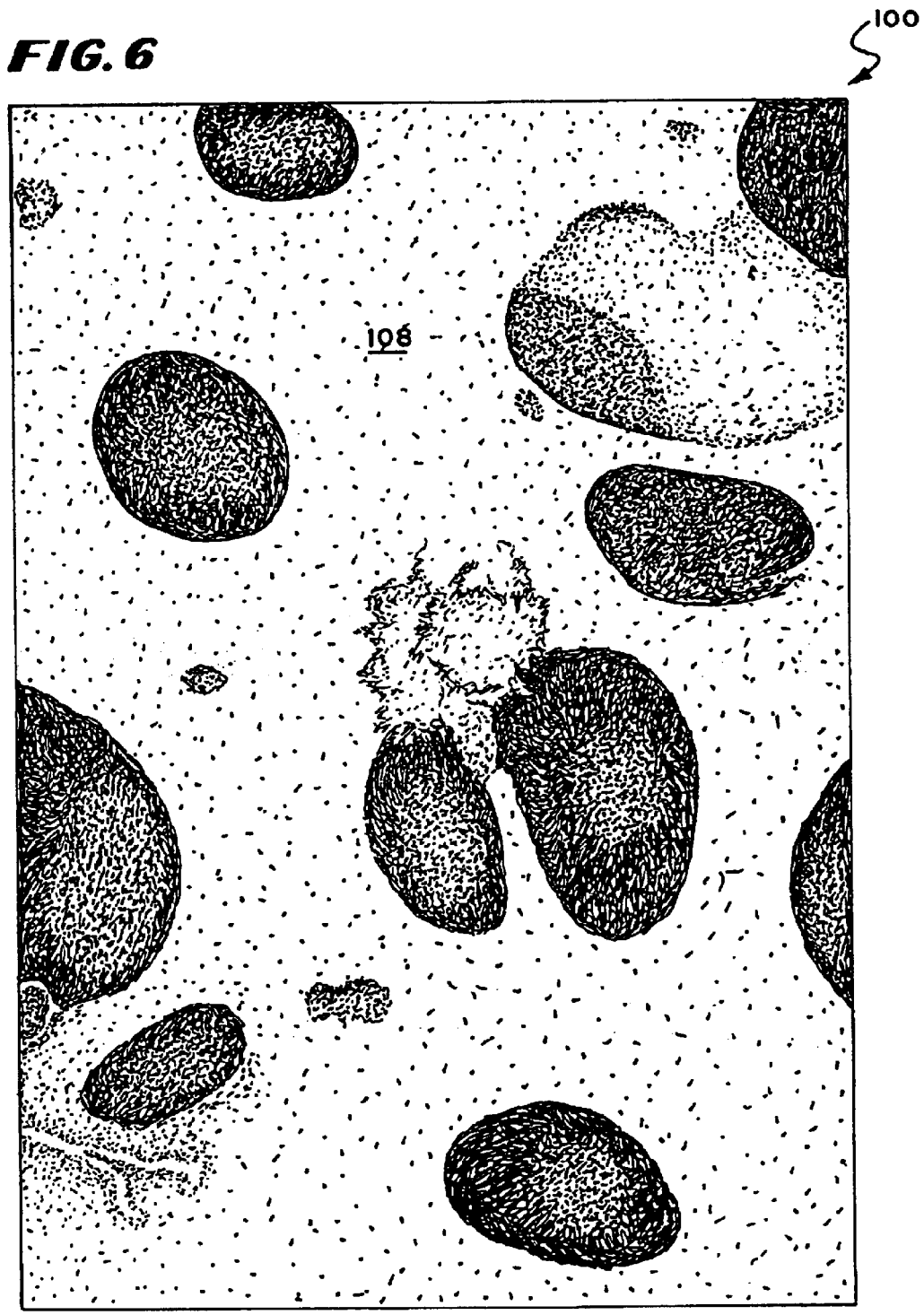
FIG. 6 is a plane SEM view (×1.5) of the upstream skin surface of the membrane shown in FIG. 4.

The main filter region MF comprises a membrane 100 that removes leukocytes. With reference to FIGS. 4 to 6, the membrane 100 of the main filter region MF can be characterized as follows:

(i) as FIG. 4 shows, in side section, the membrane 100 possess an interior porous structure formed by intersecting cells 102 having a range of diameters, with interior apertures 104 formed by intersections of the cells 102, (ii) as FIG. 4 also shows, the diameters of the cell 102 can be grouped into two general regions: larger diameter cells 102 adjacent to one skin surface 108 (which FIG. 6 shows in plane view) and smaller diameter cells 102 adjacent to the other skin surface 106 (which FIG. 5 shows in plane view). It is not believed important as to whether the blood flow is from skin surface 108 to 106, or vice versa, (iii) as FIG. 5 shows, the cells 102 intersect the skin surface 106, forming pores 110, and (iv) the majority of the skin surface 106 occupied by the pores 110 (i.e., the total open area if the skin surface 106 shown in FIG. 5) is formed by pores 110 having a diameter of between about 12 μm to about 28 μm.

Alternatively, the main filter region MF can comprise alternating layers of isotropic membranes of small and large pore size. The main filter region MF thus comprises a layered porous membrane structure that includes regions of larger pore sizes alternating in the direction of flow with regions of smaller pore sizes, or vice versa. Blood traversing the main filter region thereby passes in succession through alternating regions of smaller, then larger pores, or vice versa.

In a preferred embodiment, the membrane 100 is made of a polyethersulfone (PES) material, which can be obtained from Osmonics, Inc. (Minnetonka, Minn.).

To achieve a 3 to 4 log reduction in the number of leukocytes carried in unit of whole blood (typically between 2×109 to 6×109) without plugging, the total surface area of the membrane 100 forming the main filter region MF should be between about 500 cm2 and about 1500 cm2.

In a preferred arrangement, PES membranes 100 are arranged in multiple individual layers, each individual layer having the characteristics listed above, which together forming the main filter region MF. Blood traversing the multiple layers of the main filter region MF thereby encounter alternating regions of large pore size and then small pore size and then large pore size and then small pore size, etc, or vice versa. This serial transition between large and small pore size regions along the flow path create successive changes in the flow dynamics of the blood and are believed to enhance leukocyte removal.

The assembly of the layered PES membranes in the main filter region MF, in association with a prefilter region PRF, a transfer filter region TFR, and a postfilter region POF, as above described, provides a filter 20 that allows the passage of upwards to 90% to 95% of platelets contained in a unit of whole blood, while achieving a 3 to 4 log reduction in the number of leukocytes. The filter 20 is therefore well suited for inclusion in multiple blood bag systems in which whole blood is filtered to remove leukocytes before centrifugation, as will be described.

In forming the filter 20, a unitary, continuous peripheral seal 36 (see FIG. 3) is formed by the application of pressure and radio frequency heating in a single process to the two sheets 32 and 34 and filtration medium 28. The seal 36 joins the two sheets 32 and 34 to each other, as well as joins the filtration medium 28 to the two sheets 32 and 34. The seal 36 integrates the material of the filtration medium 28 and the material of the plastic sheets 32 and 34, for a reliable, robust, leak-proof boundary. Since the seal 36 is unitary and continuous, the possibility of blood shunting around the periphery of the filtration medium 28 is eliminated.

The filter 20 also includes inlet and outlet ports 38 and 40 (see FIG. 3). The ports 38 and 40 comprise tubes made of medical grade plastic material, like PVC-DEHP. As FIG. 2 shows, the ports 38 and 40 comprise separately molded parts that are heat sealed by radio frequency energy over a hole 40 formed in the sheets 32 and 34 before the unitary peripheral seal 36 is formed.

Figure 7:
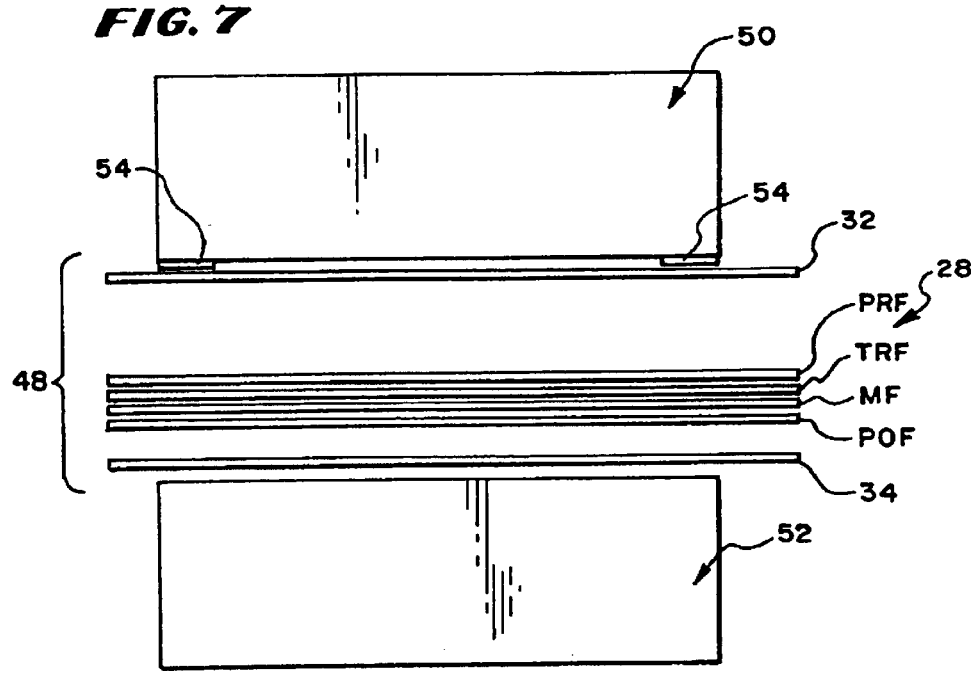
FIG. 7 is a side section view of the pre-assembled form of the filter shown in FIG. 3, located between two spaced apart radio frequency energy dies.
Figure 8:
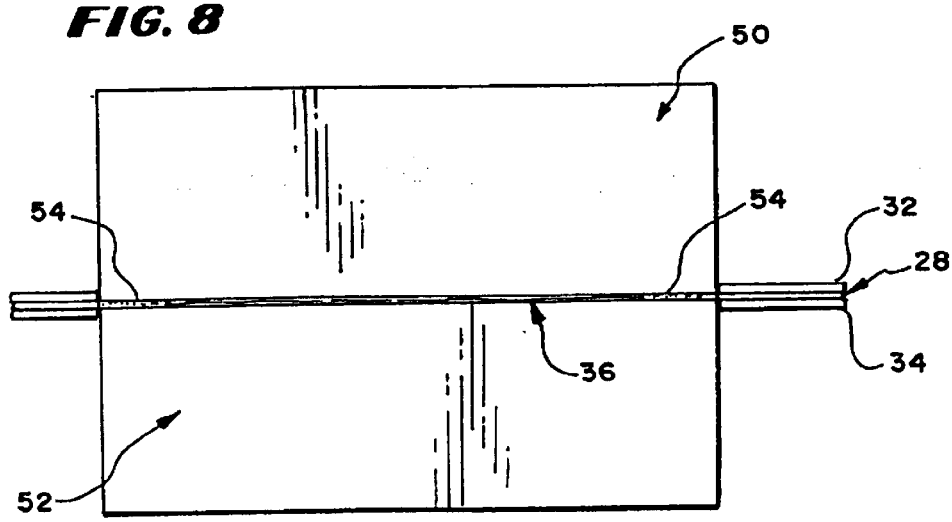
FIG. 8 is a side section view of the pre-assembled form of the filter shown in FIG. 3, engaged by the dies, which apply radio frequency energy to form a unitary peripheral seal.

The filter 20 (see FIG. 7) is formed by sandwiching layers of the prefilter region PRF, transfer filter region TFR, main filter region MF, and postfilter region POF between the first and second plastic sheets 32 and 34. The layered filter pre-assembly is placed between a pair of opposed dies 50 and 52 (as FIG. 7 shows). The opposed dies 50 and 52 are moved together (see FIG. 8), to apply pressure to press the peripheral edge of the pre-assembly 48 together. Preferably a stop 54 is provided to accurately space the dies 50 and 52 apart from each other.

As the dies 50 and 52 apply pressure about the peripheral edge, RF energy is applied through the dies 50 and 52. The combination of RF energy and pressure softens the plastic material of the sheets 32 and 34. The applied pressure causes the heat softened material of the sheets 32, 34 to penetrate the interstices of the filtration medium 28, creating an interior matrix of sheet material commingled with filtration medium material. Within the matrix, the filtration medium melts, creating a composite seal 36.

At its surface, along the sheets 32 and 34, the seal 36 comprises mostly the material of the sheets 32 and 34. With increasing distance from the surface, the seal 36 comprises a commingled melted matrix of the material of the sheets 32 and 34 and the material of the filtration medium 28. This is believed to occur because the sheet material, which is electrically heated and caused to flow by the applied radio frequency energy, is further caused by the applied pressure to flow into and penetrate the interstices of the medium 28. The heated sheet material that flows under pressure into the interstices of the medium 28 causes the medium 28 itself to melt about it.

After a brief period of cooling, the seal 36 sets and the dies 50 and 52 are withdrawn. In a representative embodiment, the dies 50 and 52 are coupled to a 4 KW radio frequency energy generator. Pressure of 60 PSI is applied, maintaining a die gap of 1.2 mm. A sealing time of about 5.5 seconds is realized, followed by a cooling time of about 5 seconds.

Figure 9:
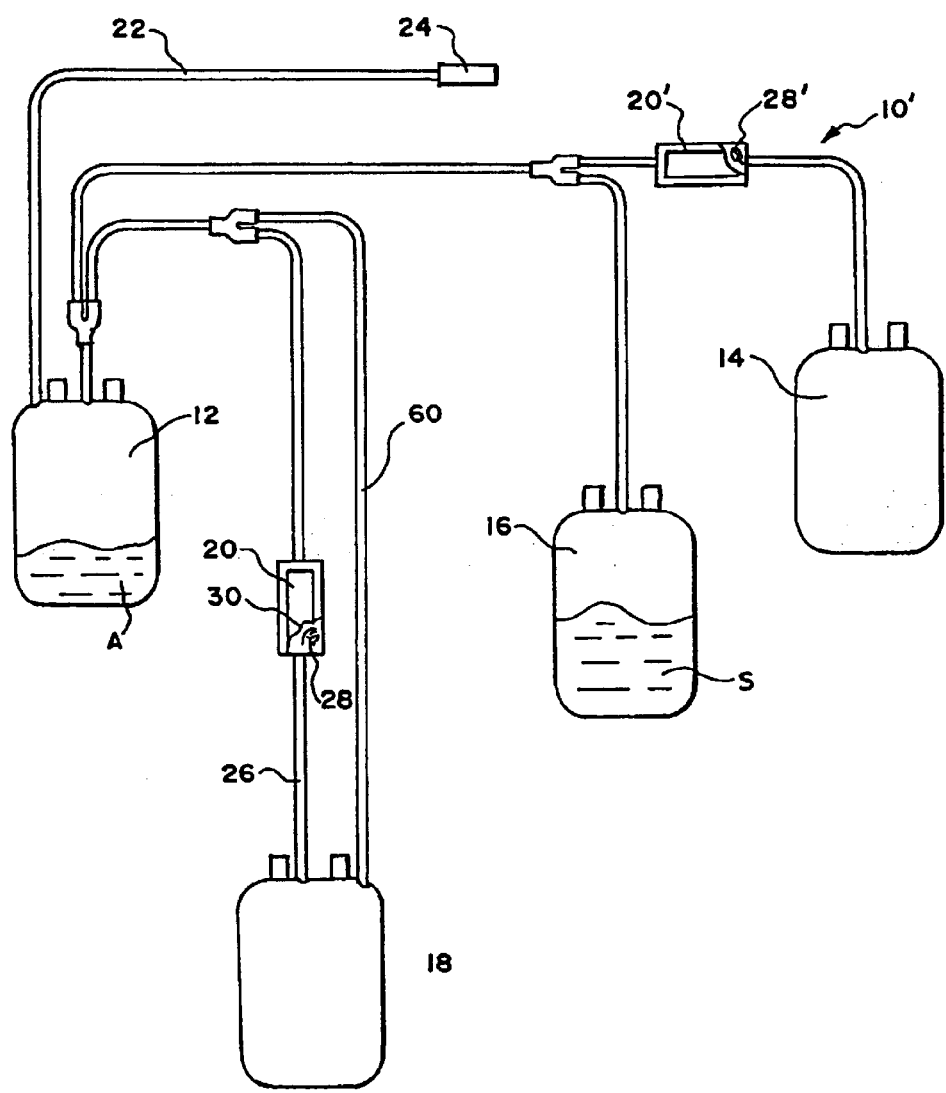
FIG. 9 is a schematic view of a blood collection and storage system that includes two integral filters that embody features of the invention, one to remove leukocytes from red blood cells and the other to remove leukocytes from platelet-rich plasma.

A flexible filter can be integrated in different ways into multiple blood bag systems. For example (see FIG. 9), a system 10' like that shown in FIG. 1 can include a second integral flexible filter 20' in-line between the primary bag 12 and the transfer bag 14. In this arrangement, the filtration medium 28' is selected to remove leukocytes from platelet-poor plasma prior to entering the transfer bag 14.

Figure 10:
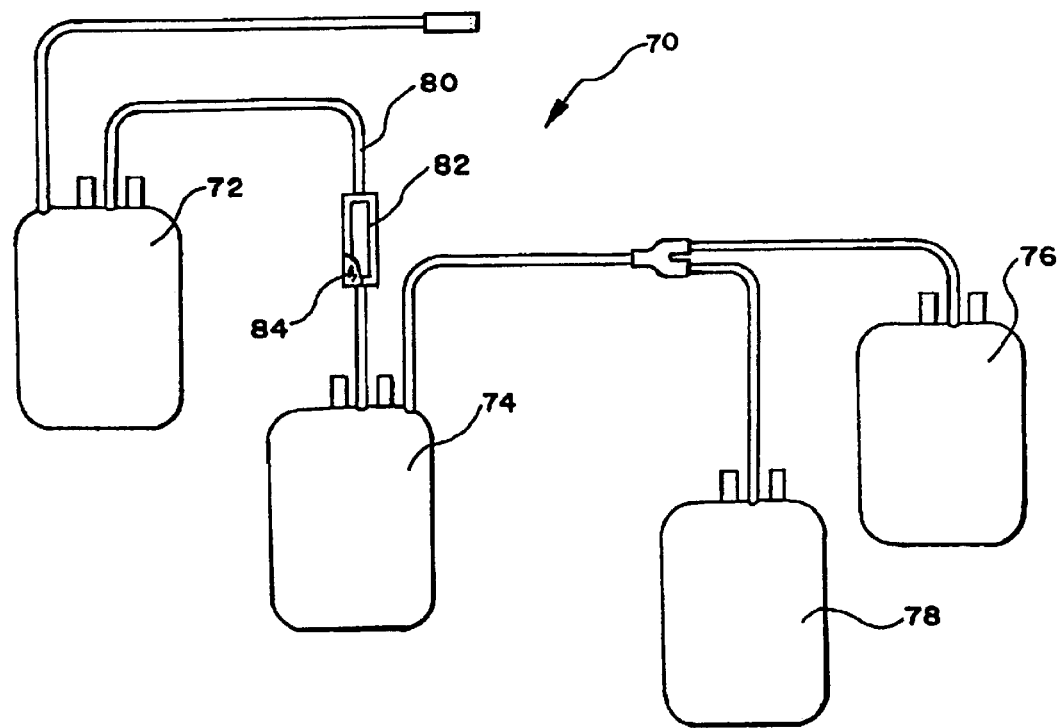
FIG. 10 is a schematic view of a blood collection and storage system that includes a filter that embodies features of the invention to remove leukocytes from whole blood prior to centrifugal processing.

As another example, FIG. 10 shows a system 70 that includes a primary bag 72 and transfer bags 74, 76, 78. The primary bag 72 receives whole blood from a donor. The whole blood is transferred from the primary bag 72 through tubing 80 into the transfer bag 74. The tubing 80 carries in-line an integral, flexible filter 82 of the type previously described. The filtration medium 84 is selected to remove leukocytes from the whole blood, without also removing platelets or red blood cells. The leukocyte-depleted whole blood is centrifugally processed in the transfer bag 74 into red blood cells and platelet-rich plasma, both of which are in a leukocyte-depleted condition.

The transfer bag 76 receives the leukocyte-depleted platelet-rich plasma, leaving the leukocyte-depleted red blood cells in the transfer bag 74 for storage. The platelet-rich plasma is centrifugally separated by conventional means in the transfer bag 76 into platelet concentrate and platelet-poor plasma. The platelet-poor plasma is transferred into the transfer bag 78 for storage. This leaves the platelet concentrate in the transfer bag 76, which serves as its storage container.

The flexible filter that embodies the invention avoids the handling and processing problems rigid filter housings have presented in the past. Unlike a rigid housing, the flexible housing 30 will not puncture associated bags, which are also made of flexible plastic materials. Unlike a rigid housing, the flexible housing 30 conforms and is compliant to stress and pressures induced during use.

The close proximity of the flexible sheet 32 and the filtration medium 28 on the inlet side of the filter 20 creates a capillary effect, which promotes displacement of air and automatic priming of the filter 30 under the fluid head pressure of gravity flow from a source container. The fluid head pressure causes the flexible sheet 32 to distend or expand after priming. It thus creates a natural pressure manifold, which evenly distributes the fluid across the inlet face of the filtration medium 28. This assures that entrapped air is vented and that the fluid flows through the filtration medium 28 under uniform pressure and distribution.

As the fluid container empties, negative pressure is created downstream of the filter 20. Because the inlet and outlet sheets 32 and 34 of the housing 30 are flexible, they will collapse around the space occupied by the filtration medium 28, minimizing the amount of residual blood left in the filter 30 after use. Fluid drains from the outlet side without the use of an auxiliary air vent.

Furthermore, the flexible housing 30 will not crack during heat sterilization. The flexible housing 30 also does not impede heat penetration during heat sterilization processes. Instead, the housing 30 accommodates uniform heat penetration into the filtration medium 28. The filter 20 can undergo sterilization at the same time the entire system 10 is sterilized, making a one-step sterilization process possible.

Various features of the invention are set forth in the following claims.

We claim:

1. A method of filtering blood comprising:

providing a filter comprising a housing, and a filter media in the housing including a main filter region comprising a layered non-fibrous membrane structure including a plurality of adjacent non-fibrous membrane layers, each adjacent non-fibrous membrane layer having a first skin surface and a second skin surface, an interior porous structure formed between the first and second skin surfaces by intersecting cells having a range of diameters, the cells adjacent to the first skin surface having diameters generally smaller than the diameters of the cells adjacent to the second skin surface, the first skin surface including an open area comprising pores formed by cells intersecting the first skin surface, the majority of the open area being defined by pores having a diameter of between about 12 $\mu$m and 28 $\mu$m, the layered non-fibrous membrane structure being arranged so that the first skin surface of one non-fibrous membrane layer adjoins the second skin surface of an adjacent non-fibrous membrane layer, introducing blood from a source of blood into said filter, passing said blood in succession through alternating regions of smaller and then larger intersecting cells, a fibrous prefilter region upstream of the main filter region sized to remove gross clots and aggregates present in blood, and a fibrous postfilter region downstream of the main filter region sized to provide a fluid manifold, thereby removing leukocytes from said blood.

2. A method of filtering blood comprising according to claim 1, said method further comprising passing said blood into a container following said step of removing leukocytes from said blood.

* * * * *